(12) United States Patent
Yin et al.

(10) Patent No.: US 9,079,183 B2
(45) Date of Patent: *Jul. 14, 2015

(54) MAGNETIC MICROPLATE ASSEMBLY

(71) Applicant: QIAGEN GAITHERSBURG, INC., Gaithersburg, MD (US)

(72) Inventors: Fei Yin, North Potomac, MD (US); Bandele Jeffrey-Coker, Gaithersburg, MD (US)

(73) Assignee: QIAGEN GAITHERSBURG, INC., Gaithersburg, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/841,991

(22) Filed: Mar. 15, 2013

(65) Prior Publication Data

US 2013/0315800 A1      Nov. 28, 2013

Related U.S. Application Data

(63) Continuation of application No. 12/480,044, filed on Jun. 8, 2009.

(60) Provisional application No. 61/131,272, filed on Jun. 9, 2008.

(51) Int. Cl.
*B01L 9/00* (2006.01)
*G01N 35/00* (2006.01)
*B01L 3/00* (2006.01)

(52) U.S. Cl.
CPC ............ *B01L 9/523* (2013.01); *G01N 35/0098* (2013.01); *B01L 3/5085* (2013.01); *B01L 2200/025* (2013.01); *B01L 2300/0829* (2013.01)

(58) Field of Classification Search
CPC ........................... B01L 2200/025; B01L 9/523
USPC ................................................... 422/560, 561
See application file for complete search history.

(56) References Cited

U.S. PATENT DOCUMENTS 3,917,331 A    11/1975   Duran
4,438,068 A     3/1984   Forrest
(Continued)

FOREIGN PATENT DOCUMENTS

DE    10 2006 049 135        4/2008
EP              2285493 A2    2/2011
(Continued)

OTHER PUBLICATIONS

"Sample & Assay Technologies", Qiagen Product Guide 2008, Section 10.2, p. 451.
(Continued)

*Primary Examiner* — Paul Hyun
(74) *Attorney, Agent, or Firm* — Miles and Stockbridge PC

(57) ABSTRACT

Magnetic microplate assemblies are disclosed for assaying of biological activated magnetic particles from a supernatant. The assemblies include a magnetic microplate holder and a microplate including a plurality of wells for retaining the magnetic particles. The microplate holder includes a plurality of magnets for attracting the magnetic particles to the wells and a plurality of detents for securing the microplate in the holder. The detents allow the microplate to be tightly retained in the holder when the assembly is turned over to discard supernatant and wash buffer applied to rinse supernatant from the magnetic particles.

21 Claims, 8 Drawing Sheets

(56) References Cited

U.S. PATENT DOCUMENTS

| | | | |
|---|---|---|---|
| 4,710,472 | A | 12/1987 | Saur et al. |
| 4,910,148 | A | 3/1990 | Sorensen et al. |
| 4,988,618 | A | 1/1991 | Li et al. |
| 5,186,827 | A | 2/1993 | Liberti et al. |
| 5,200,084 | A | 4/1993 | Liberti et al. |
| 5,458,785 | A | 10/1995 | Howe et al. |
| 5,779,907 | A | 7/1998 | Yu |
| 5,897,783 | A | 4/1999 | Howe et al. |
| 5,976,369 | A | 11/1999 | Howe et al. |
| 6,426,050 | B1 | 7/2002 | Pham et al. |
| 8,647,593 | B2 | 2/2014 | Yin et al. |
| 2002/0131167 | A1 | 9/2002 | Nguyen et al. |
| 2002/0146832 | A1 | 10/2002 | Michel et al. |
| 2006/0210435 | A1 | 9/2006 | Alavie et al. |

FOREIGN PATENT DOCUMENTS

| | | |
|---|---|---|
| WO | 91/08312 | 6/1991 |
| WO | 01/60519 | 8/2001 |
| WO | 02/18052 | 3/2002 |
| WO | 02/26384 | 4/2002 |
| WO | 03/022440 | 3/2003 |
| WO | 2009152092 A2 | 12/2009 |

OTHER PUBLICATIONS

Mittendorf et al.; "HPV-DNA-Diagnostik Zur Zervixkarzinomfrueherkennung: Deutsche Agentur Fuer HTA Des Deutschen Instituts Fuer Medizinisch Dokumentation Und Information," 1 Auflage 2007.

Nanda et al.; "Accuracy of the Papanicolaou Test in Screening for and Follow-Up of Cervical Cytologic Abnormalities: A Systematic Review, Annals of Internal Medicine," 132(10):810-819; May 16, 2000.

Davey et al.; "Introduction and Commentary, Strategic Science Symposium, Human Papillomavirus Testing—Are You Ready for a New Era in Cervical Cancer Screening?," Arch Pathol Lab Med. 127: 927-929, Aug. 2003.

Malloy et al.; "HPV DNA Testing: Technical and Programmatic Issues for Cervical Cancer Prevention in Low-Resource Settings," Path, Dec. 2000.

Stacey et al.; "Translation of the Human Papillomavirus Type 16 E7 Oncoprotein From Bicistronic MRNA is Independent of Splicing Events Within the E6 Open Reading Frame," Journal of Virology, 69(11):7023-7031; Nov. 1995.

Hsu et al.; Quantification of HPV-16 E6-E7 Transcription in Cervical Intraepithelial Neoplasia by Reverse Transcriptase Polymerase Chain Reaction, Int. J. Cancer: 55, 397-401 (1993).

Bohms et al.; "The Predominant MRNA Class in HPV16-Infected Genital Neoplasias Does Not Encode the E6 or the E7 Protein," Int. J. Cancer: 55, 791-798 (1993).

Middleton et al.; "Organization of Human Papillomavirus Productive Cycle During Neoplastic Progression Provides a Basis for Selection of Diagnostic Markers," Journal of Virology, Oct. 2003, pp. 10186-10201.

Stoler et al.; "Human Papillomavirus Type 16 and 18 Gene Expression in Cervical Neoplasias," Human Pathol. 23 (1992), pp. 117-128.

Higgins et al.; "Transcription Patterns of Human Papillomavirus Type 16 in Genital Intraepithelial Neoplasia: Evidence for Promoter Usage Within the E7 Open Reading Frame During Epithelial Differentiation," J. Gen. Virol. 73 (1992), pp. 2047-2057.

Karlsen et al.; "Use of Multiple PCR Primer Sets for Optimal Detection of Human Papillomavirus," J. Clin. Microbiol. 34 (1996), pp. 2095-2100.

Parks et al.; "Physical Status and Expression of HPV Genes in Cervical Cancers," Gynec. Oncol. 95 (1997), pp. 121-129.

Broker et al.; "A Molecular Portrait of Human Papillomavirus Carcinogenesis," Cancer Cells 7 (1989), pp. 197-207.

Letter to EPO Dated Jan. 6, 2010 Regarding EP 1 038 022 (46 Pages).
Letter to EPO Dated Mar. 2, 2009 Regarding EP 1 038 022 (15 Pages).
Letter to EPO Dated Oct. 6, 2008 Regarding EP 1 038 022 (27 Pages).
Letter to EPO Dated Aug. 8, 2008 Regarding EP 1 038 022 (11 Pages).
EPO Decision Dated May 27, 2008 Regarding Opposition of EP 1 038 022 (19 Pages).
Letter to EPO Dated Jan. 25, 2008 Regarding EP 1 038 022 (10 Pages).
Letter to EPO Dated Jan. 23, 2008 Regarding EP 1 038 022 (6 Pages).
Communication from EPO Dated May 14, 2007 Regarding EP 1 038 022 (8 Pages).
Letter to EPO Dated Oct. 4, 2006 Regarding EP 1 038 022 (11 Pages).
Letter to EPO Dated Apr. 18, 2006 Regarding EP 1 038 022 (10 Pages).
International Preliminary Report on Patentability and Written Opinion of PCT/US2009/046613, Mailed Dec. 23, 2010 (11 Pages).
International Search Report; PCT/US2009/046613; Feb. 10, 2010 (7 Pages).

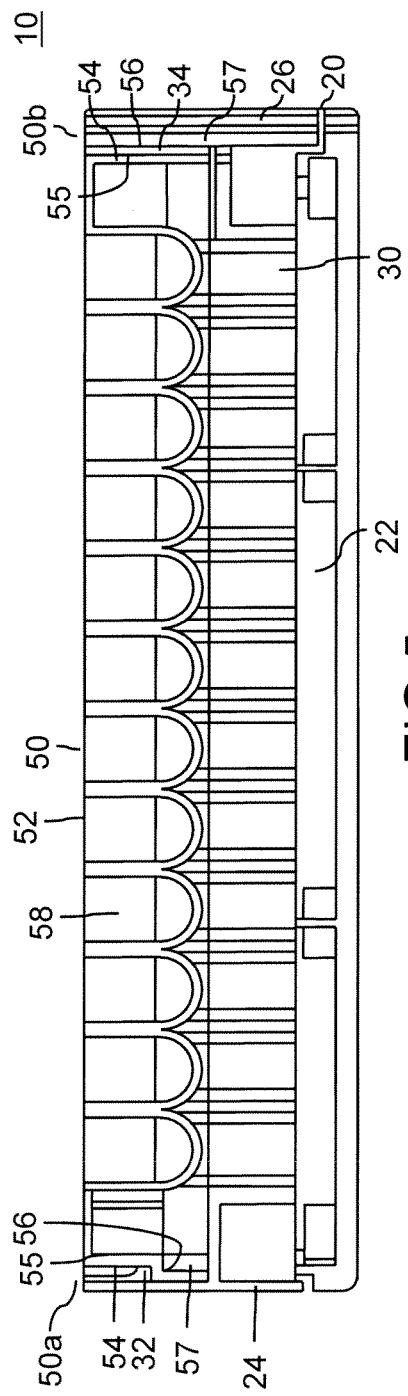
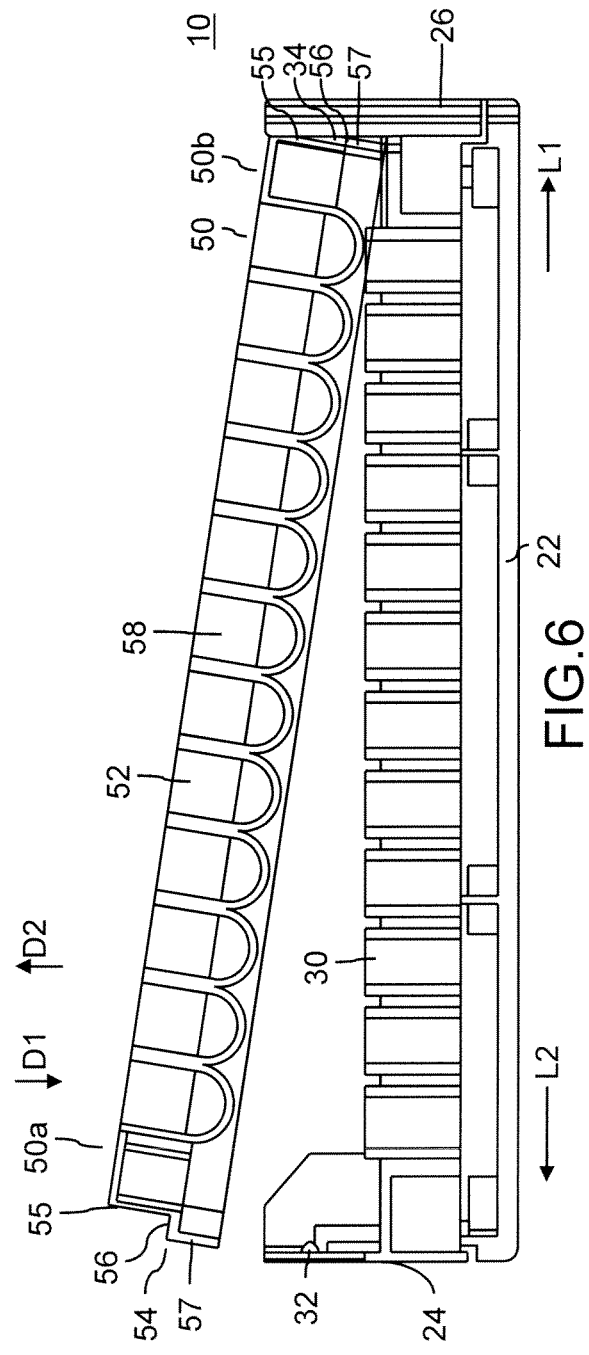
FIG.5
FIG.6

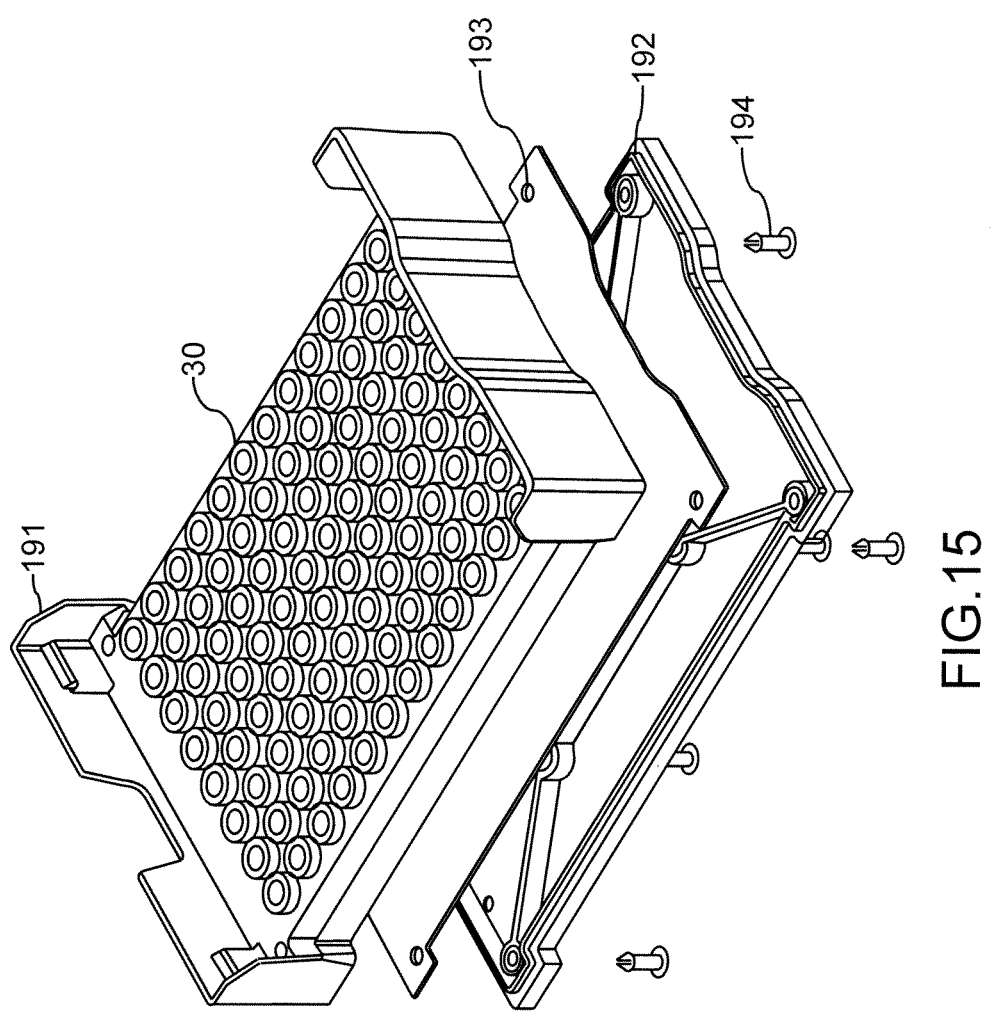

MAGNETIC MICROPLATE ASSEMBLY

RELATED APPLICATIONS

This application is a Continuation of U.S. application Ser. No. 12/480,044, filed Jun. 8, 2009, which claims the benefit of U.S. Provisional Application No. 61/131,272, filed on Jun. 9, 2008, the entire contents of which are incorporated by reference.

BACKGROUND

This disclosure relates to an improved magnetic microplate assembly for biological agent separation and purification.

The use of biological activated magnetic particles or beads as carriers for biological agent separation and purification is well known. Several hand-held magnetic microplate assemblies are commercially available for separating biological activated magnetic beads from a supernatant and assaying the beads. Such separators may include a magnet base and a microplate having a plurality of wells (typically six, twelve, twenty-four, forty-eight or ninety-six wells) for retaining biological activated magnetic beads attracted by the base. In order to assay biological activated magnetic beads, the beads are delivered to the wells in a supernatant, and the beads are attracted to and retained in the wells by the magnet base. The supernatant is separated from the beads and discarded by inverting the microplate such that the upper surface of the microplate generally faces downward. A wash buffer may thereafter be applied to wash the beads in the wells, and the wash buffer may be discarded by inverting the microplate.

During the process of inverting the microplate to discard the supernatant and the wash buffer, the microplate and the magnet base must be held together in order to prevent the loss of any magnetic beads from the wells. In some known magnetic microplate assemblies, the magnet base and the microplate are held together with one or more rubber bands that are wrapped around the magnet base and the microplate. Because the rubber bands tend to trap supernatant and wash buffer and tend to shift their positions during the washing step, the rubber bands can cause cross-contamination of assays.

It is therefore desirable to provide a magnetic microplate assembly that includes improved means for securing the microplate during inversion of the assembly for discarding supernatant and wash buffer.

SUMMARY

Magnetic microplate assemblies are disclosed for separating biological activated magnetic particles from a supernatant. The assemblies include a magnetic microplate holder and a microplate including a plurality of wells for retaining the magnetic particles. The microplate holder includes a plurality of magnets for attracting the magnetic particles to the wells and a plurality of detents for securing the microplate in the holder. The detents allow the microplate to be tightly retained in the holder when the assembly is turned over to discard supernatant and wash buffer applied to rinse supernatant from the magnetic particles.

According to one embodiment, the detents of the microplate holder comprise a plurality of catches or rib members disposed on end walls of the microplate holder and positioned to engage a flange of the microplate to secure the microplate in the microphage holder.

According to another embodiment, the detents of the microplate holder comprise a plurality of resilient detents disposed in end walls of the microplate holder and a plurality of dowel pins disposed near one of the end walls, wherein the resilient detents and dowel pins are positioned to engage a flange of the microplate to secure the microplate in the microplate holder.

Methods of loading a microplate in a microplate holder and unloading a microplate from a microplate holder are also disclosed.

Further features and advantages of the invention will be apparent upon reference to the following description, appended drawings and claims.

BRIEF DESCRIPTION OF THE DRAWINGS

FIG. 5 is a side cross-sectional view taken along line A-A of FIG. 1;

FIG. 6 is a side cross-sectional view illustrating methods of loading the microplate in the microplate holder and unloading the microplate from the microplate holder in the embodiment of FIGS. 1-5;

FIG. 15 is an exploded view of the magnetic microplate assembly.

DETAILED DESCRIPTION

Figure 1:
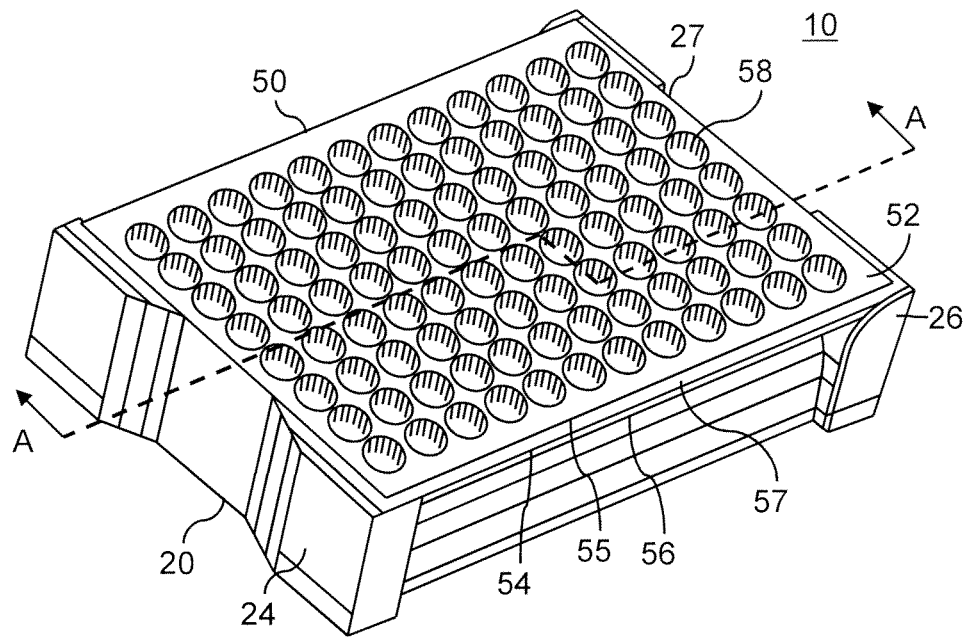
FIG. 1 is a perspective view of a magnetic microplate assembly including a microplate and a magnetic microplate holder according to one embodiment.

FIGS. 1-6 illustrate a magnetic microplate assembly 10 according to a first embodiment. Referring to FIGS. 1-5, the assembly 10 includes a magnetic microplate holder 20 and a microplate 50 retained in the holder 20. The assembly 10 is configured to separate biological activated magnetic particles or beads (not shown) from a supernatant (not shown) to enable assaying of the particles or the supernatant.

The microplate 50 is formed from a single member which has an upper platform 52, a perimeter wall 54 extending downward from the upper platform 52, and multiple wells 58 integrally formed in the upper platform 52 for holding liquid samples. The perimeter wall 54 includes an upper wall portion 55 and a stepped-out bottom flange 57 including a horizontal ledge or lip 56 joined to the upper wall portion 55. As shown, the wells 58 in the microplate 50 are arranged in an eight-by-twelve array, thereby forming a ninety-six well plate. However, it should be understood that any other number of wells, such as six, twelve, twenty-four, forty-eight, three hundred eighty-four or fifteen hundred thirty-six or any other number may be provided, and various array designs may be employed. The microplate 50 may be constructed of non-magnetic plastic or other suitable materials.

Figure 3:
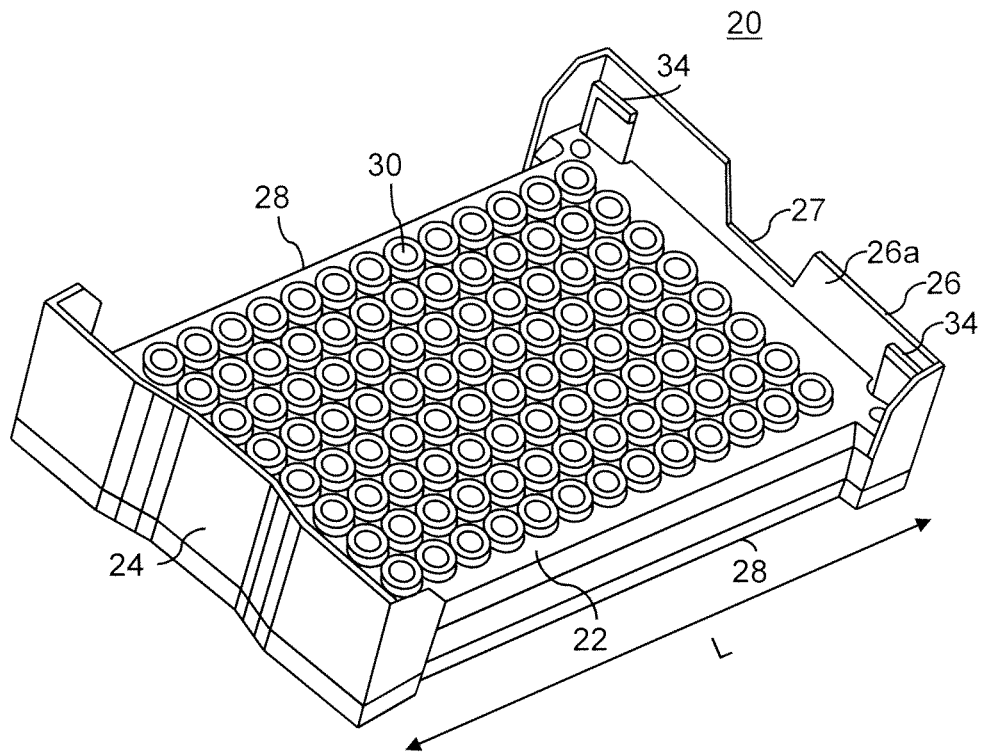
FIG. 3 is a perspective view of the microplate holder of FIGS. 1 and 2.
Figure 4:
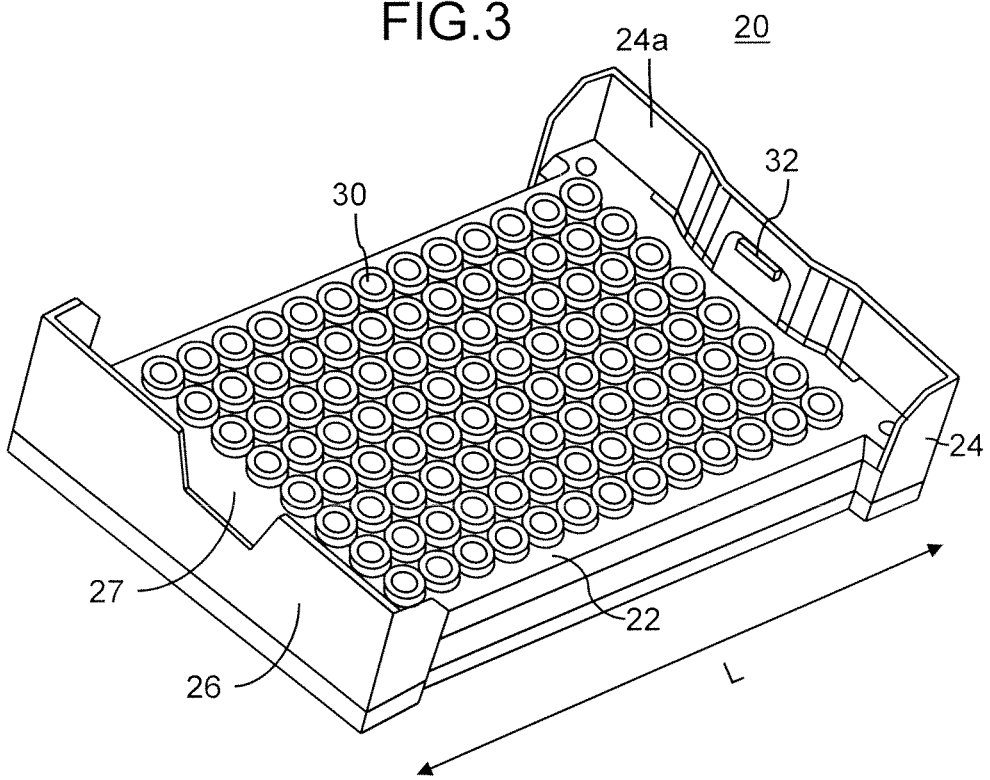
FIG. 4 is another perspective view of the microplate holder of FIGS. 1 and 2.

Turning to FIGS. 3 and 4, the microplate holder 20 includes a bottom wall 22, a first end wall 24 formed at a first end of the bottom wall 22, and a second end wall 26 formed at a second end of the bottom wall 22, and substantially open side sections 28. The holder 20 is may be constructed of non-magnetic plastic, however, other materials may be used. A plurality of cylindrical magnets 30 are positioned in the bottom wall 22. In the embodiment shown, the microplate holder includes ninety-six magnets 30 arranged in an eight-by-twelve array, with each magnet 30 being positioned for alignment directly below a well 58 of the microplate 50. However, it should be understood that other numbers and arrangements of magnets are possible. For example, embodiments may be employed in which there are fewer magnets 30 than wells 58, and each magnet 30 is positioned for alignment with a group of multiple wells 58. Additionally, the number of magnets 30 employed may vary based on the number of wells 58 provided in the microplate 50.

Referring still to FIGS. 3 and 4, the end wall 26 includes a cut-out portion 27 which allows a user to grab an end portion of the microplate 50 during loading of the microplate 50 into the microplate holder 20, as well as during unloading of the microplate 50 from the microplate holder 20. The substantially open side sections 28 allow a user to grab side portions of the microplate 50 and also serve to prevent liquid accumulation in the assembly 10 during washing of the microplate 50. The end walls 24, 26 are flexible and resilient in the longitudinal direction L, to allow loading of the microplate 50 into the holder 20 and unloading of the microplate 50 from the holder 20, as is described in detail in following paragraphs.

As shown in FIGS. 3-6, the microplate holder 20 includes a plurality of detents or catches 32, 34 protruding from the interior surfaces 24a, 26a of the end walls 26 for engaging the microplate 50 and retaining the microplate 50 in the microplate holder 20. The catches 32, 34 may be rib members or other elements suitable for engaging and retaining the microplate 50. The catches 32, 34 may be located at a height above the bottom wall 22 that allows the bottom flange 57 of the microplate 50 to be tightly secured below the catches 32, 34, as will be described in greater detail in following paragraphs. Referring to FIGS. 1-4, a single catch 32 is provided at a laterally central area of the end wall 24, and two catches 34 are provided near opposite lateral ends of the end wall 26. However, it should be understood that the number and location of the catches 32, 34 can vary as desired.

Figure 2:
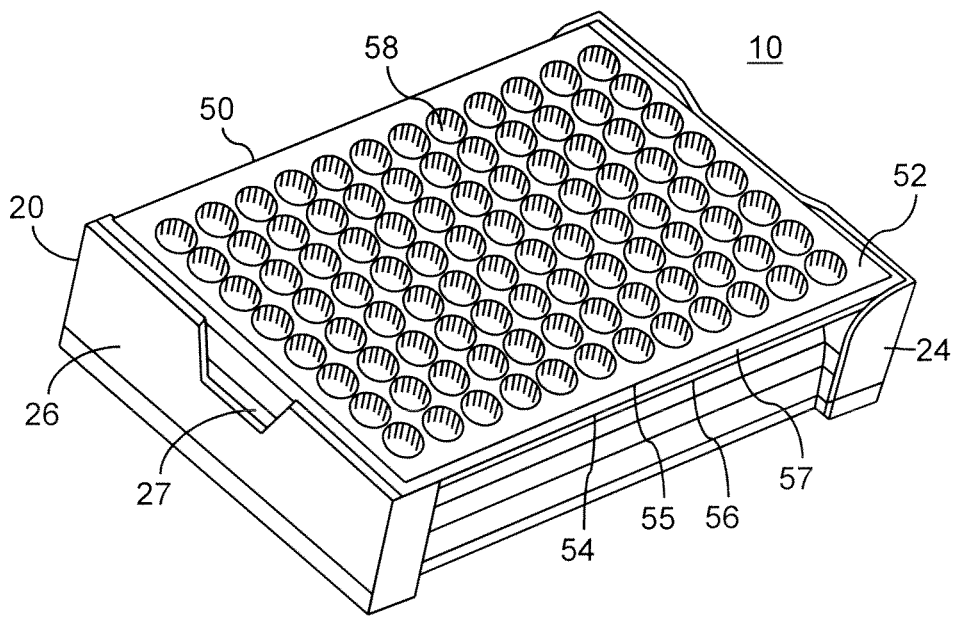
FIG. 2 is another perspective view of the microplate assembly of FIG. 1.

FIGS. 1, 2 and 5 show the microplate assembly 10 in a fully assembled configuration, wherein the microplate 50 is secured in the holder 20. In the assembled configuration, the bottom flange 57 of the perimeter wall 54 is retained under the catches 32, 34 at ends 50a, 50b of the microplate 50. More specifically, the ledge 56 is positioned under and engages the undersides of the catches 32, 34 at ends 50a, 50b, thereby preventing vertical movement of the microplate 50 during use. In order to separate biological activated magnetic particles from a supernatant, the supernatant is delivered into the wells 58, and the particles are retained in the wells 58 under the force of magnetic fields generated by the magnets 30. The supernatant can be discarded by inverting or tilting the assembly 10 such that the upper platform 52 of the microplate 50 is turned downward. A wash buffer (not shown) may thereafter be applied to the microplate 50 to wash residual supernatant away from the upper platform 52 and the particles in the wells 58. The wash buffer may then be discarded by inverting or tilting the assembly 10. Due to the catches 32, 34 preventing vertical movement of the microplate 50 within the holder 20, the microplate 50 is securely retained close to the magnets 30 within the holder 20 during inversion or tilting of the assembly 10, thereby allowing the particles to remain within the wells 58.

FIG. 6 illustrates how the microplate 50 can be loaded into the holder 20. As shown in FIG. 6, the microplate 50 can be loaded into the holder 20 by: tilting the end 50b of the microplate 50 slightly downward in the direction D1; sliding the microplate 50 longitudinally forward in the direction L1 such that the flange 57 is positioned under the catches 34 at the end 50b and the ledge 56 engages the undersides of the catches 34 at the end 50b; pressing the end 50b against the end wall 26 so as to flex the end wall 26 outward in the direction L1 from its natural position and thereby allowing the end 50a to move longitudinally in the direction L1 inside of the catch 32; pressing the end 50a down in the direction D1 such that the flange 57 travels downward past the catch 32 at the end 50a; and then releasing the microplate 50 such that the end wall 26 returns to its natural position and forces the microplate 50 to slide longitudinally backward in the direction L2 such that the flange 37 is positioned under the catch 32 at the end 50a and the ledge 56 engages the underside of the catch 32 at the end 50a.

Alternatively, the microplate 50 can be loaded into the holder 20 by first inserting the end 50a. Specifically, the microplate 50 can be loaded into the holder 20 by: tilting the end 50a slightly downward in the direction D1; sliding the microplate 50 backwards in the direction L2 such that the flange 57 is positioned under the catch 32 at the end 50a and the ledge 56 engages the underside of the catch 32 at the end 50a; pressing the end 50a against the end wall 24 so as to flex the end wall 24 outward in the direction L2 from its natural position and thereby allowing the end 50b to move longitudinally in the direction L2 inside of the catches 34; pressing the end 50b down such that the flange 57 travels downward past the catches 34 at the end 50b; and then releasing the microplate 50 such that the end wall 24 returns to its natural position and forces the microplate 50 to slide longitudinally forward in the direction L1 such that the flange 37 is positioned under the catches 34 at the end 50b and the ledge 56 engages the undersides of catches 34 at the end 50b.

Still referencing FIG. 6, the microplate 50 can be unloaded from the holder 20 by: flexing the end wall 26 outward in the direction L1 and/or pushing the microplate 50 in the direction L2 so as to flex the end wall 24 outward in the direction L2, such that the flange 57 is moved longitudinally inside of the catches 34 in the direction L2 at the end 50b; lifting the end 50b up in the direction D2 such that the flange 57 moves up past the catches 34 at the end 50b; sliding the microplate 50 forward in the direction L1 such that the flange 57 is moved past the catch 32 in the direction L1 at the end 50a; and then lifting the microplate 50 away from the holder 20. Alternatively, the microplate 50 may be unloaded from the holder 20 by: flexing the end wall 24 outward in the direction L2 and/or pushing the microplate 50 in the direction L1 so as to flex the end wall 26 outward in the direction L1, such that the flange 57 is moved longitudinally inside of the catch 32 in the direction L1 at the end 50a; lifting the end 50a up in the direction D2 such that the flange 57 moves up past the catch 32 at the end 50a; sliding the microplate 50 backwards in the direction L2 such that the flange 57 is moved past the catches 34 in the direction L2 at the end 50b; and then lifting the microplate 50 away from the holder 20.

FIGS. 7-12 illustrate a magnetic microplate assembly 100 according to another embodiment. Referring to FIGS. 7-11, the assembly 100 includes a magnetic microplate holder 120 and a microplate 50 retained in the holder 120.

Figure 9:
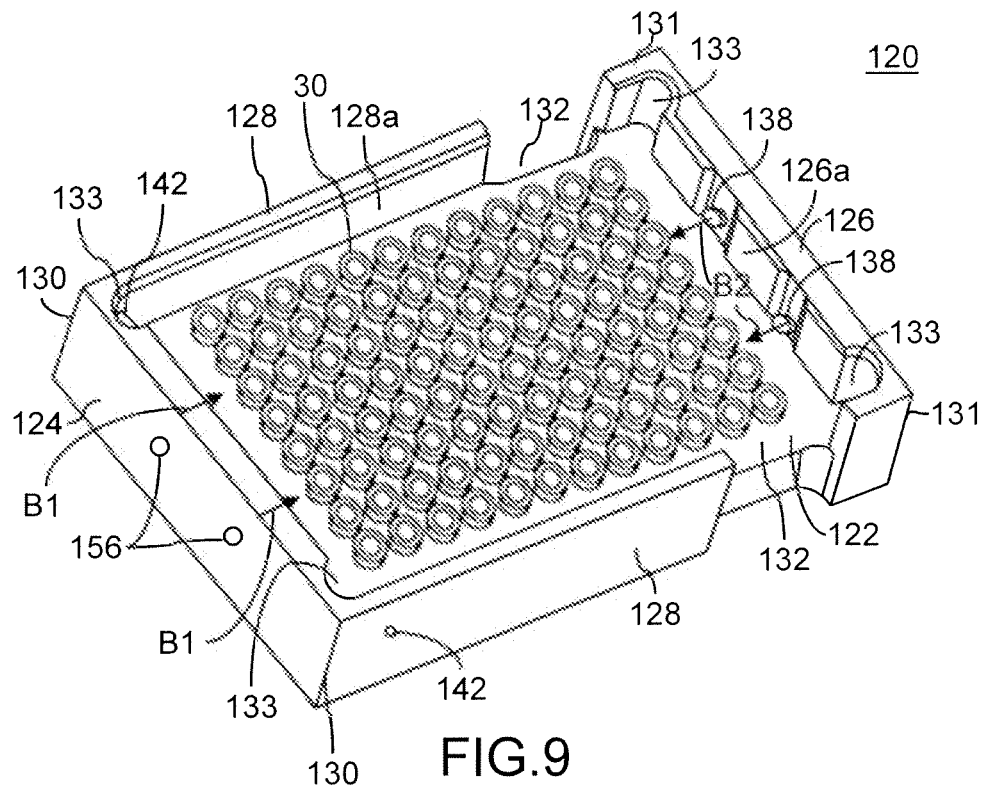
FIG. 9 is a perspective view of the microplate holder of FIGS. 7 and 8.
Figure 10:
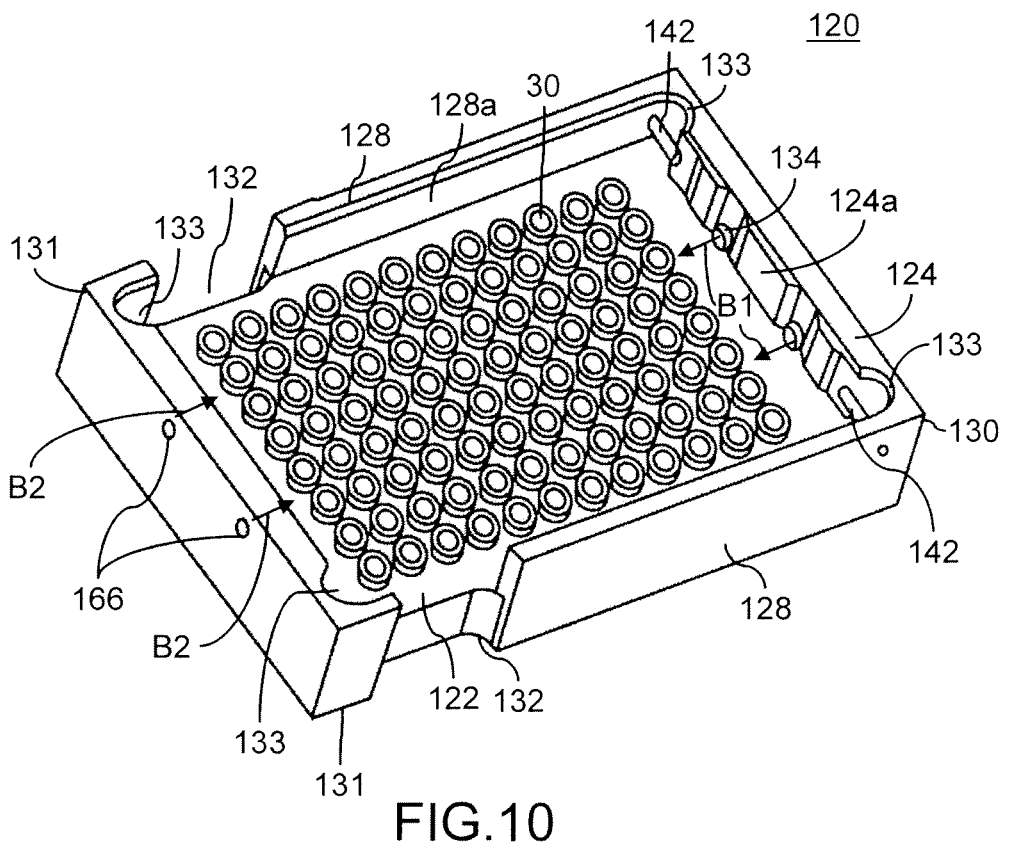
FIG. 10 is another perspective view of the microplate holder of FIGS. 7 and 8.

Turning to FIGS. 9 and 10, the microplate holder 120 includes a bottom wall 122, a first end wall 124 formed at a first end of the bottom wall 122, and a second end wall 126 formed at a second end of the bottom wall 122, and side walls 128. The holder 120 is may be constructed of non-magnetic plastic, however, other materials may be used. A plurality of cylindrical magnets 30 are positioned in the bottom wall 122, with each magnet 30 being positioned for alignment directly below a well 58 of the microplate 50. As in the previous embodiment, it should be understood that various numbers and arrangements of magnets are possible.

Still referencing FIGS. 9 and 10, the end walls 124, 126 each include a pair of recesses 133 at the corners 130, 131 where the end walls 124, 126 join the side walls 128. The recesses 133 facilitate gripping of the microplate 50 during loading and unloading of the microplate 50. The side walls 128 include open sections 132 which allow a user to grab side portions of the microplate 50 and also serve to prevent liquid accumulation in the assembly 100 during washing of the microplate 50.

As shown in FIGS. 7-12, a pair of resilient detents, or spring-and-ball plungers 134 are provided in the end wall 124. As illustrated in FIG. 13, the spring-and-ball plungers 134/138 each include a ball member 135/139 seated on a spring 136/140 which applies a biasing force B1/B2 that biases the ball member 135/139 in an extended position so as to protrude from the inner surface 124a/126a of the end wall 124/126. The ball member 135/139 and spring 136/140 are seated in a bore 150/160 in the end wall 124/126. The bore 150/160 extends entirely through the end wall 124/126, and has a first, open end 152/162 at the inner surface 124a/126a of the end wall 124/126 and a second end 154/164 an outer surface 124b/126b of the end wall 124/126. The second end 154/164 is closed by a plug 156/166. The spring 136/140 is seated against the plug 156/166. The diameter of the bore 150/160 is slightly larger than the diameter of the ball member 135/139 at the second end 154/164 and an intermediate section 155/165. The diameter of the bore 150/160 is slightly smaller than the diameter of the ball 135/139 at the first end 152/162, thereby allowing the ball member 135/139 to partially protrude from the first pen end 152/162 while being retained in the bore 150/160. Spring-and-ball plungers 134/138 can be installed in the end walls 124/126 by inserting the ball member 135/139 and the spring 136/140 through the second end 154/164 into the bore 150/160, and then securing the plug 156/166 in the second end 156/166.

Figure 14:
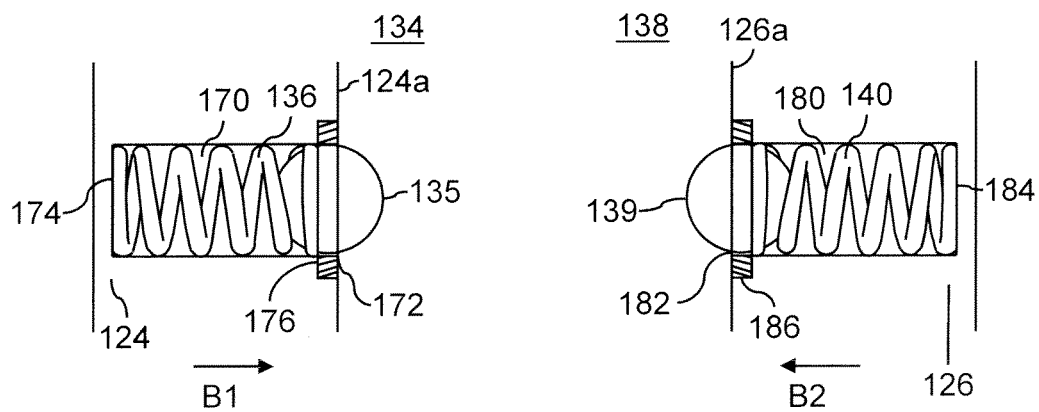

According to an alternate embodiment shown in FIG. 14, the ball member 135/139 and spring 136/140 are seated in a bore 170/180 in the end wall 124/126. The bore 170/180 extends partially through the end wall 124/126, and has an open end 172/182 at the inner surface 124a/126a of the end wall 124/126 and a closed end 174/184 against which the spring 136/140 rests at an interior portion of the end wall 124/126. The bore 170/180 has a diameter that is slightly larger than the diameter of the ball member 135/139. An annular reducer 176/186 having an inner diameter that is slightly smaller than the diameter of the ball member 135/139 is positioned at the open end 172/182, thereby allowing the ball member 135/139 to partially protrude from the open end 172/182 while being retained in the bore 170/180 by the reducer 176/186. According to this embodiment, spring-and-ball plungers 134/138 can be installed in the end wall 124/126 by inserting the ball member 135/139 and the spring 136/140 through the open end 172/182 into the bore 170/180, and then securing the annular reducer 176/186 at the open end 172/182.

Referencing FIGS. 9-12, a detent or dowel pin 142 is attached to each side wall 128 near the corners 130. The dowel pins 142 extend inwardly from inside surfaces 128a of the side walls 128 substantially parallel to the end wall 124. The spring-and-ball plungers 134, 138 and dowel pins 142 may be located at a height above the bottom wall 122 that allows the bottom flange 57 of the microplate 50 to be tightly secured below the spring-and-ball plungers 134, 138 and dowel pins 142, as will be described in greater detail in following paragraphs. As will be described later, the spring-and-ball plungers 134, 138 and dowel pins 142 cooperate to retain the microplate 50 in the holder 120. Although a pair of spring-and-ball plungers 134, 138 are shown positioned in central regions of the end walls 124, 126, and a pair of dowel pins 142 are shown near the corners 130, it should be understood that other arrangements and numbers of spring-and-ball plungers 134, 138 and/or dowel pins 142 are possible. In an alternate embodiment, the dowel pins 142 may be replaced by other elongate catch members, or by catches or rib members positioned on the end wall 124.

Figure 7:
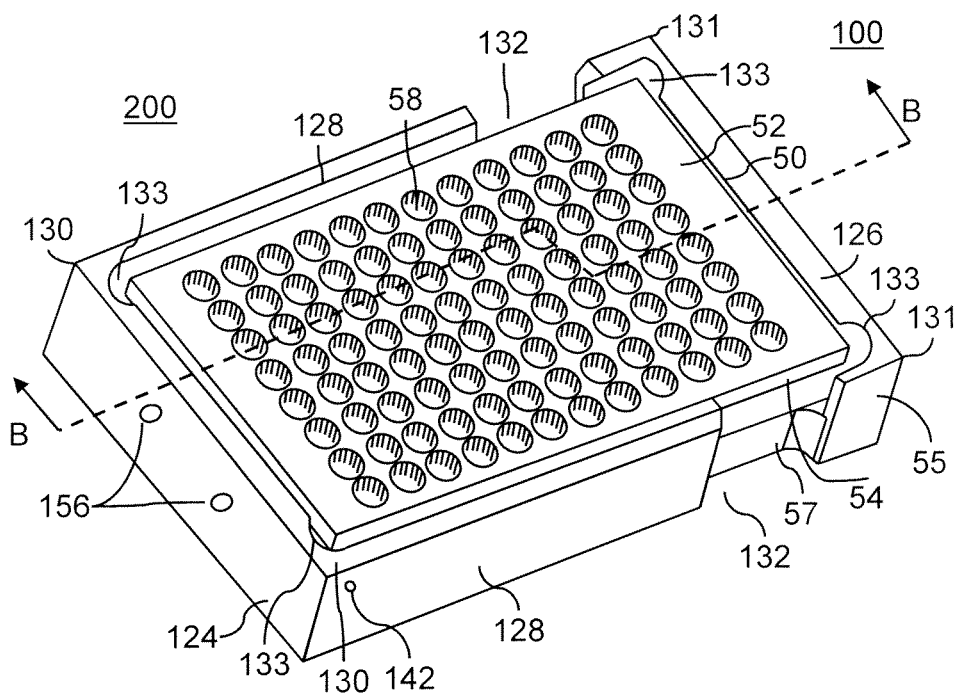
FIG. 7 is a perspective view of a magnetic microplate assembly including a microplate and a magnetic microplate holder according to another embodiment.
Figure 8:
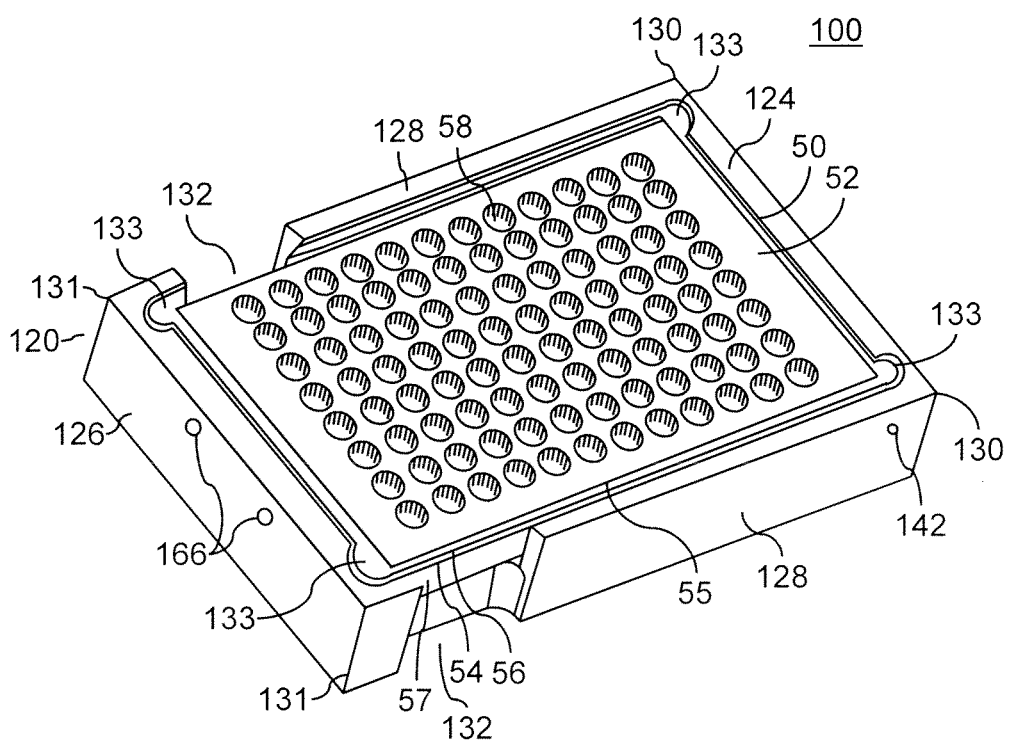
FIG. 8 is another perspective view of the microplate assembly of FIG. 7.
Figure 11:
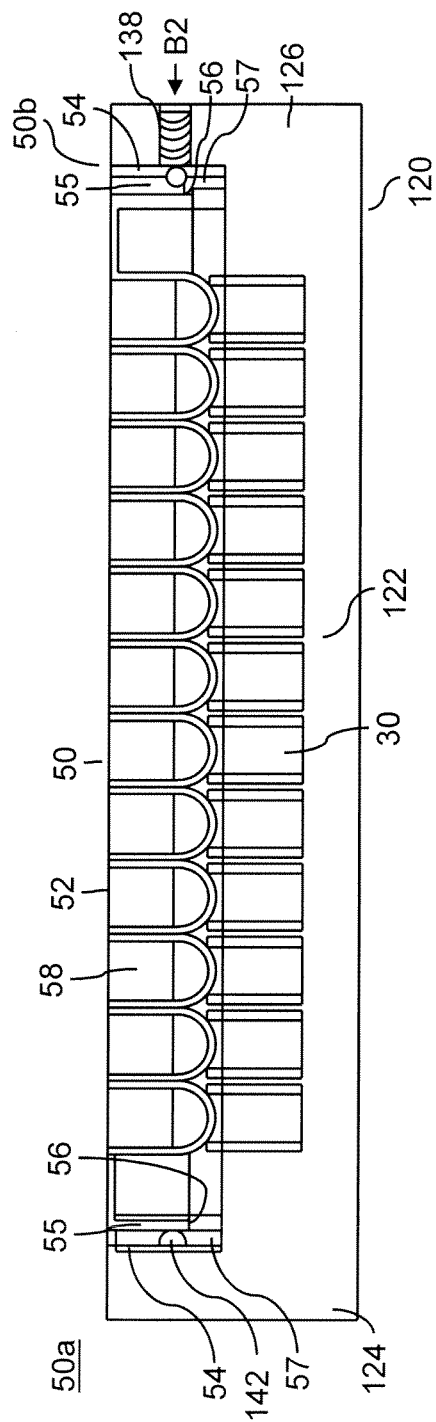
FIG. 11 is a side cross-sectional view taken along line B-B of FIG. 7.

FIGS. 7, 8 and 11 show the microplate assembly 100 in a fully assembled configuration. In this configuration, the microplate 50 is secured in the holder 120 such that the bottom flange 57 is retained under the dowel pins 142 and the spring-and-ball plungers 134, 138. Specifically, the ledge 56 engages and is positioned below the dowel pins 142 at the end 50a, and the ledge 56 engages and is positioned below the spring-and-ball plungers 134, 138 at the ends 50a, 50b, thereby preventing vertical movement of the microplate 50 during use. The assembly 100 may be used to separate biological activated magnetic particles from a supernatant in the same manner as the assembly 10 of the previous embodiment. Supernatant and wash buffer may be discarded in a manner similar to that for discarding supernatant and wash buffer from the assembly 10, that is, by tilting or inverting the assembly 100 such that the upper platform 52 of the microplate 50 is turned downward. The open sections 133 of the side walls 128 assist in draining supernatant and wash buffer from the microplate 50. Due to the spring-and-ball plungers 134 and the dowel pins preventing vertical movement of the microplate 50 within the holder 20, the microplate 50 is securely retained close to the magnets 30 within the holder 120 during inversion or tilting of the assembly 100, thereby allowing the particles to remain within the wells 58.

Figure 12:
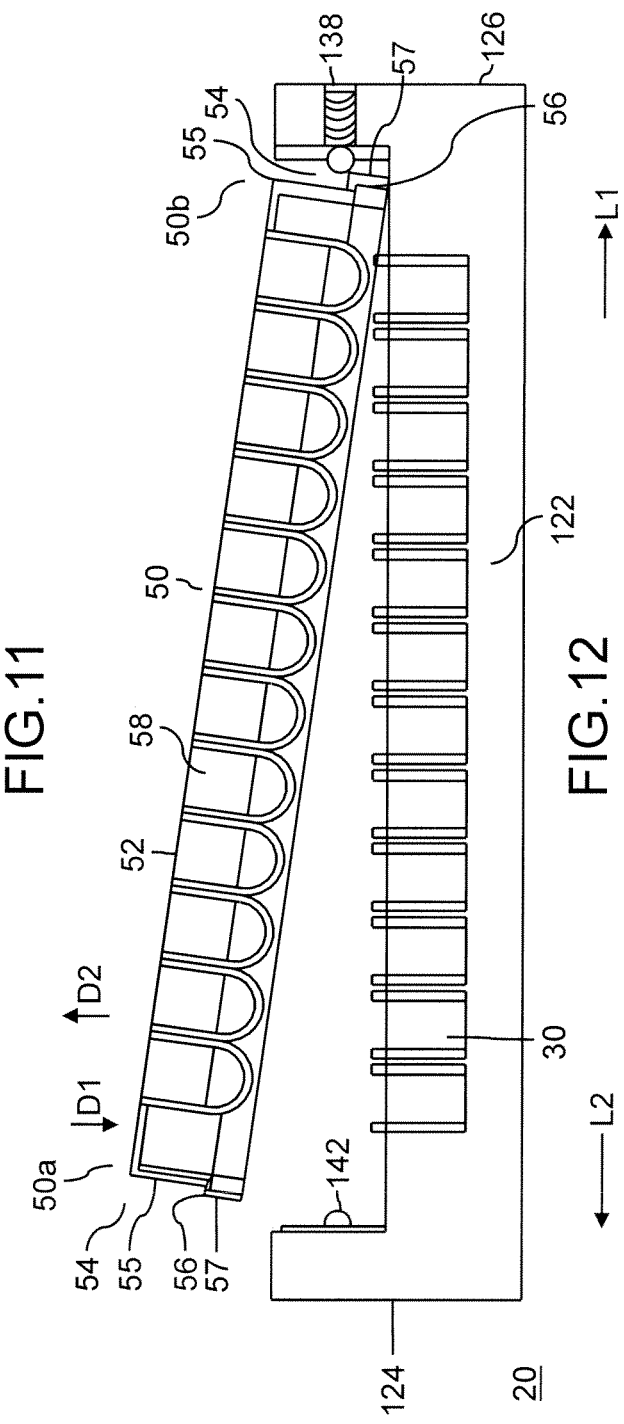
FIG. 12 is a side cross-sectional view illustrating a method of loading the microplate in the microplate holder and unloading the microplate from the microplate holder in the embodiment of FIGS. 7-11.
Figure 13:
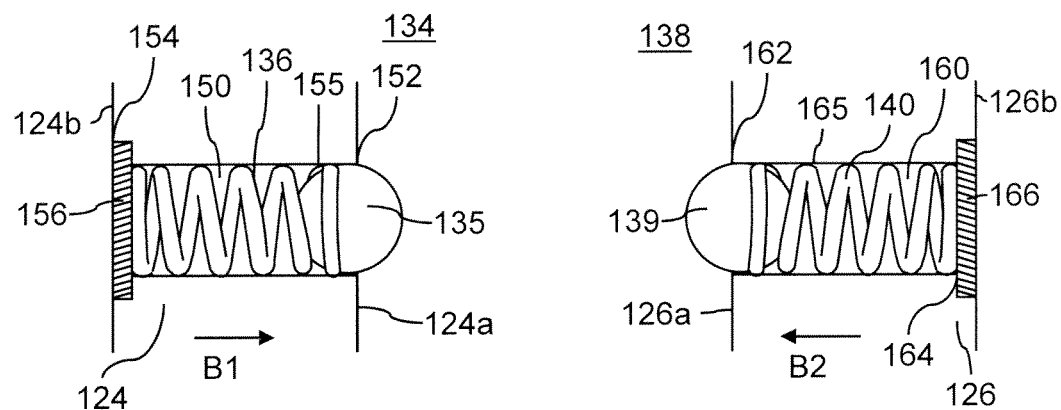
FIGS. 13 and 14 show spring-and-ball plungers employed in the embodiment of FIGS. 7-12.

FIG. 12 illustrates how the microplate 50 can be loaded into the holder 120. As shown in FIG. 12, the microplate 50 can be loaded into the holder 120 by: tilting the end 50b of the microplate 50 slightly downward in the direction Dl; sliding the microplate 50 longitudinally forward in the direction L1 such that the end 50b engages and compresses the spring-and-ball plungers 138 towards the end wall 126, the ledge 56 moves below and into engagement with undersides of the spring-and-ball plungers 138, and the flange 57 moves longitudinally inside of the dowel pins 142 and the spring-and-ball plungers 134 at the end 50a of the microplate 50; pressing the end 50a down in the direction D1 such that flange 57 travels downward past the spring-and-ball plungers 134 and the dowel pins 142 at the end 50a; and then releasing the microplate 50 such that the spring-and-ball plungers 138 return to their extended positions and force the microplate 50 to move in the direction L2 such that the ledge 56 moves under and into engagement with the undersides of the spring-and-ball plungers 134 and the dowel pins 142 at the end 50a.

Alternatively, the microplate 50 can be loaded into the holder 120 by first inserting the end 50a. Specifically, the microplate 50 can be loaded into the holder 120 by: tilting the end 50a of the microplate 50 slightly downward in the direction D1; sliding the microplate 50 longitudinally forward in the direction L2 such that the end 50a engages and compresses the spring-and-ball plungers 134 towards the end wall 124, the ledge 56 moves below and into engagement with undersides of the spring-and-ball plungers 134 and the dowel pins 142, and the flange 57 moves longitudinally inside of the spring-and-ball plungers 138 at the end 50b of the microplate 50; pressing the end 50b down in the direction D1 such that flange 57 travels downward past the spring-and-ball plungers 138 at the end 50b; and then releasing the microplate 50 such that the spring-and-ball plungers 134 return to their extended positions and force the microplate 50 to move in the direction L1 such that the ledge 56 moves under and into engagement with the undersides of the spring-and-ball plungers 138.

Still referring to FIG. 12, the microplate 50 can be unloaded from the holder 120 by: pressing the end 50b forward in the direction L1 against the spring-and-ball plungers 138 to compress the spring-and-ball plungers 138 towards the wall 126 and cause the flange 57 to move inside of the dowel pins 142 and the spring-and-ball plungers 134 at the end 50a; lifting the end 50a upward in the direction D2 such that the flange 57 moves up past the dowel pins 142 and the spring-and-ball plungers 134 at the end 50a; sliding the microplate 50 backwards in the direction L2 such that the flange 57 is moved inside of the spring-and-ball plungers 138 at the end 50b; and then lifting the microplate 50 away from the holder 120. Alternatively, the microplate 50 can be unloaded from the holder 120 by: pressing the end 50a backward in the direction L2 against the spring-and-ball plungers 134 to compress the spring-and-ball plungers 134 towards the wall 124 and cause the flange 57 to move inside of the spring-and-ball plungers 138 at the end 50b; lifting the end 50b upward in the direction D2 such that the flange 57 moves up past the spring-and-ball plungers 138 at the end 50b; sliding the microplate 50 forward in the direction L1 such that the flange 57 is moved inside of the spring-and-ball plungers 138 and the dowel pins 142 at the end 50a; and then lifting the microplate 50 away from the holder 120.

In FIG. 15, an exploded view of the microplate holder 20 provides an example of its construction. The upper portion of the plate holder 191 contains each of the individual magnets 30. A bottom plate 192 attaches to the top section of the plate holder 191 and is held by pins 194. Pins 194 may be constructed of plastic, metal or any material suitable for securing the plates sections 191 and 192. Pins may be any fastening hardware suitable for attaching bottom plate 192 with plate holder top section 191. Between these plate sections 191 and 192 is a metallic plate 193 which holds magnets 30 to the upper plate section 191 through magnetic force. Although magnets 30 may be secured to 191 by adhesive, friction or other suitable means, the metallic plate 193 is sufficient to keep 30 in place. Similarly, the metallic plate 30 is held in place by the magnets but also may be attached to either 191, 192 or both by the use of an adhesive, friction or other suitable means. The plate 193 may be made from any ferromagnetic material, or may be itself magnetic. Plate 193 may be excluded from microplates where magnets 30 are secured to the top plate section 191 by adhesive, friction or other suitable means, although plate 193 may still be included in the assembly to provide further securing of the magnets 30.

The foregoing disclosure provides illustrative embodiments of the invention and is not intended to be limiting. It should be understood that modifications of the disclosed embodiment are possible within the spirit and scope of the invention, and the invention should be construed to encompass such modifications.

What is claimed is:

1. A microplate assembly for assaying biological material, comprising:
   a microplate comprising:
      wells for holding biological particles,
      an upper platform, the wells being located in the upper platform,
      a perimeter wall extending downward from the upper platform and including an upper wall portion and a stepped-out bottom flange; and
   a microplate holder for retaining the microplate, the microplate holder comprising:
      a bottom wall comprising at least one magnet,
      a first end wall located at a first end of the bottom wall,
      a second end wall located at a second end of the bottom wall; and
      at least one first detent comprising a catch located on an inner surface of the first end wall; and
      at least one second detent comprising a second catch located on an inner surface of the second end wall,
   wherein the catch of the at least one first detent and the catch of the at least one second detent on the microplate holder are arranged to engage the bottom flange on the microplate, thereby securing the microplate in the microplate holder,
   wherein the first end wall or the second end wall on the microplate holder comprises a cut-out portion suitable for gripping the microplate, and
   wherein the microplate holder comprises substantially open side portions extending between the first end wall and the second end wall, wherein the substantially open side portions are positioned to allow a user to grab side portions of the microplate,
   wherein the catch of the at least one first detent and the catch of the at least one second detent on the microplate holder retain the microplate within the microplate holder during inversion or tilting of the microplate assembly, and
   wherein the bottom wall further comprises:
      a third end of the bottom wall between the first end of the bottom wall and the second end of the bottom wall; and
      a fourth end of the bottom wall, opposite the third end, and arranged between the first end of the bottom wall and the second end of the bottom wall,
   wherein the open side portions extend across the entire third end and the entire fourth end of the bottom wall.

2. The microplate assembly of claim 1, wherein the at least one first detent and the at least one second detent are arranged to engage a substantially horizontal surface of the microplate.

3. The microplate assembly of claim 1, wherein the bottom flange includes a horizontal ledge joined to the upper wall portion, and wherein the at least one first detent and the at least one second detent are arranged to engage the horizontal ledge.

4. The microplate assembly of claim 1, wherein the first end wall and the second end wall are flexible and resilient, so as to allow end portions of the microplate to be inserted under and removed from under the at least one first detent and the at least one second detent.

5. The microplate assembly of claim 1, wherein the catch of the at least one first detent and the catch of the at least one second detent on the microplate holder prevent vertical movement of the microplate during use.

6. A microplate assembly for assaying biological material, comprising:
  a microplate comprising wells for holding biological particles; and
  a microplate holder for retaining the microplate, the microplate holder comprising:
    a bottom wall,
    a first end wall located at a first end of the bottom wall,
    a second end wall located at a second end of the bottom wall,
    a pair of side walls extending between the first end wall and the second end wall, wherein at least one of the pair of side walls comprises an open section suitable for gripping and for draining liquid from the microplate,
    at least one first resilient detent located on an inner surface of the first end wall, the at least one first detent being compressible towards the first end wall,
    at least one second resilient detent located on an inner surface of the second end wall, the at least one first detent being compressible towards the second end wall, and
    a pair of catch members located near or on the first end wall,
  wherein the microplate comprises:
    an upper platform, the wells being located in the upper platform; and
    a perimeter wall extending downward from the upper platform and including an upper wall portion and a stepped-out bottom flange, and
  wherein the at least one first resilient detent, the at least one second resilient detent, and the catch members are arranged at a height above the bottom wall to engage the microplate and secure the bottom flange on the microplate below the first resilient detent, the second resilient detent, and the catch members on the microplate holder.

7. The microplate assembly of claim 6, wherein the microplate holder comprises at least one magnet located in the bottom wall.

8. The microplate assembly of claim 6, wherein the at least one first resilient detent and the at least one second resilient detent each comprise a ball-and-spring plunger.

9. The microplate assembly of claim 6, wherein the catch members comprise dowel pins extending from the side walls.

10. The microplate assembly of claim 6, wherein the at least one first resilient detent, the at least one second resilient detent and the catch members are arranged to engage the bottom flange on the microplate, wherein the bottom flange comprises a substantially horizontal surface of the microplate.

11. The microplate assembly of claim 6, wherein the bottom flange of the microplate includes a horizontal ledge joined to the upper wall portion, and wherein the at least one first resilient detent, the at least one second resilient detent and the catch members are arranged to engage the horizontal ledge.

12. The microplate assembly of claim 6, wherein the at least one first resilient detent and the at least one second resilient detent allow end portions of the microplate to be inserted under and removed from under the at least one first resilient detent, the at least one second resilient detent and the catch members.

13. The microplate assembly of claim 6, comprising recesses located at corners of the microplate holder, the recesses allowing gripping of the microplate.

14. A microplate holder suitable for holding a microplate for assaying biological material, the microplate holder comprising:
  a bottom wall,
  a first end wall located at a first end of the bottom wall,
  a second end wall located at a second end of the bottom wall,
  a pair of side walls extending between the first end wall and the second end wall, wherein at least one of the pair of side walls comprises an open section suitable for gripping and for draining liquid from the microplate,
  at least one first resilient detent located on an inner surface of the first end wall, the at least one first detent being compressible towards the first end wall,
  at least one second resilient detent located on an inner surface of the second end wall, the at least one first detent being compressible towards the second end wall, and
  a pair of catch members located near or on the first end wall,
  wherein the microplate comprises:
    an upper platform, the wells being located in the upper platform; and
    a perimeter wall extending downward from the upper platform and including an upper wall portion and a stepped-out bottom flange, and
  wherein the at least one first resilient detent, the at least one second resilient detent, and the catch members are arranged at a height above the bottom wall to engage the microplate and secure the bottom flange on the microplate below the first resilient detent, the second resilient detent, and the catch members on the microplate holder.

15. The microplate holder of claim 14, comprising at least one magnet located in the bottom wall.

16. The microplate holder of claim 14, wherein the at least one first resilient detent and the at least one second resilient detent each comprise a ball-and-spring plunger.

17. The microplate holder of claim 14, wherein the catch members comprise dowel pins extending from the side walls.

18. The microplate holder of claim 14, wherein the at least one first resilient detent, the at least one second resilient detent and the catch members are arranged to engage a substantially horizontal surface of the microplate.

19. The microplate holder of claim 14, wherein the microplate holder is suitable for holding a microplate wherein the bottom flange of the microplate includes a horizontal ledge joined to the upper wall portion, and wherein the at least one first resilient detent, the at least one second resilient detent and the catch members are arranged to engage the horizontal ledge.

20. The microplate holder of claim 14, wherein the at least one first resilient detent and the at least one second resilient detent allow end portions of the microplate to be inserted under and removed from under the at least one first resilient detent, the at least one second resilient detent and the catch members.

21. The microplate holder of claim 14, comprising corners and recesses located at the corners, the recesses allowing gripping of the microplate.

* * * * *